United States Patent
Seitz et al.

(10) Patent No.: US 6,768,025 B2
(45) Date of Patent: Jul. 27, 2004

(54) BENZOYLCYCLOHEXANEDIONE DERIVATIVES AND THEIR USE AS HERBICIDES

(75) Inventors: Thomas Seitz, Viernheim (DE);
Andreas van Almsick, Karben (DE);
Lothar Willms, Hofheim (DE);
Thomas Auler, Bad Soden (DE);
Hermann Bieringer, Eppstein (DE);
Hubert Menne, Hofheim Ts. (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/116,297

(22) Filed: Apr. 4, 2002

(65) Prior Publication Data
US 2003/0060651 A1 Mar. 27, 2003

(30) Foreign Application Priority Data

Apr. 7, 2001 (DE) .......................... 101 17 503

(51) Int. Cl.$^7$ .......................... C07C 49/79; C07C 41/00; C07C 319/00; A01N 47/06
(52) U.S. Cl. .......................... 568/331; 568/337; 568/630; 568/633; 568/634; 568/63; 568/64; 504/306; 504/310; 504/348
(58) Field of Search .......................... 568/63, 64, 331, 568/337, 630, 633, 634; 504/310, 348

(56) References Cited

U.S. PATENT DOCUMENTS

| | | | |
|---|---|---|---|
| 4,780,127 A | | 10/1988 | Michaely et al. |
| 5,152,826 A | * | 10/1992 | Knudsen |
| 5,306,695 A | * | 4/1994 | Stark et al. |
| 5,318,947 A | | 6/1994 | Ort et al. |
| 6,376,429 B1 | * | 4/2002 | Van Almsick et al. |

FOREIGN PATENT DOCUMENTS

| | | |
|---|---|---|
| DE | 101 13 137 C2 | 1/2003 |
| EP | 0 563 817 | 10/1993 |
| EP | 0 319 075 | 7/1994 |
| EP | 0 791 572 | 8/1997 |
| WO | WO 91/05470 | 5/1991 |
| WO | WO 92/07837 | 5/1992 |
| WO | WO 92/13833 | 8/1992 |
| WO | WO 96/22958 | 8/1996 |

* cited by examiner

*Primary Examiner*—Samuel Barts
*Assistant Examiner*—Sikarl A. Witherspoon
(74) *Attorney, Agent, or Firm*—Frommer Lawrence & Haug LLP

(57) ABSTRACT

Benzoylcyclohexanedione derivatives of the formula (I) and their use as herbicides are described.

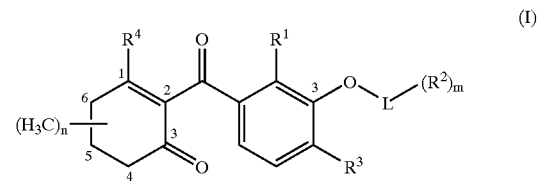

In this formula (I), $R^1$, $R^3$, and $R^4$ are various radicals, $L-(R^2)_n$ is haloalkyl, and n is 0 to 2.

13 Claims, No Drawings

BENZOYLCYCLOHEXANEDIONE DERIVATIVES AND THEIR USE AS HERBICIDES

The invention pertains to the technical field of herbicides, particularly that of herbicides for selective control of broadleaf and grass weeds in crops.

It is already known from various publications that certain benzoylcyclohexanediones possess herbicidal properties. For instance, EP-A 0 319 075, WO 92/07837, and WO 96/22958 disclose benzoylcyclohexanediones having a haloalkoxy radical in position 3 of the phenyl ring. EP-A 0 563 817 describes salts of benzoylcyclohexanediones which likewise carry a haloalkoxy radical in position 3 of the phenyl ring. WO 91/05470, WO 92/13833, and U.S. Pat. No. 4,780,127 specify benzoylcyclohexanediones which in the 3 position of the phenyl ring may be unsubstituted or may be substituted by a variety of radicals, among them trafluoromethoxy. In addition, the last-mentioned document names the compounds 2-(3-(2,3-dibromopropoxy)-2-chloro-4-ethylsulfonylbenzoyl)-1,3-cyclohexanedione and 2-(2-chloro-3-(3-chloropropoxy)-4-ethylsulfonylbenzoyl)-1,3-cyclohexanedione.

The herbicidal activity of the compounds known from these publications, however, is frequently inadequate. It is an object of the present invention to provide herbicidally active compounds possessing herbicidal properties which—relative to those of the compounds disclosed in the state of the art—are improved.

It has now been found that benzoylcyclohexanedione derivatives whose phenyl ring is substituted in position 3 by selected radicals from the $C_1$–$C_4$ haloalkoxy group are especially suitable for use as herbicides. The present invention accordingly provides compounds of the formula (I) or salts thereof

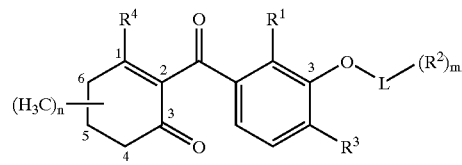

in which

L is a saturated carbon chain having 1, 2, 3 or 4 carbon atoms;

$R^1$ is iodine, bromine, chlorine, fluorine, $C_1$–$C_4$ alkyl, $C_1$–$C_4$ alkylthio, $C_1$–$C_4$ alkoxy or $C_1$–$C_4$ haloalkyl;

$R^2$ is bromine, chlorine, iodine or fluorine;

$R^3$ is bromine, chlorine, fluorine, cyano, nitro, $C_1$–$C_4$ alkyl, methylsulfonyl or ethylsulfonyl;

$R^4$ is $OR^5$ or $SR^5$;

$R^5$ is hydrogen, $C_1$–$C_4$ alkyl, $C_2$–$C_4$ alkenyl, $C_2$–$C_4$ alkynyl, benzyl or phenyl;

m is an integer from 1 to 9, and n is 0, 1 or 2, with the proviso that
a) the radical O—L—$(R^2)_m$ is not to be trifluoromethoxy, and
b) the compounds 2-(3-(2,3-dibromopropoxy)-2-chloro-4-ethylsulfonylbenzoyl)-1,3-cyclohexanedione and 2-(2-chloro-3-(3-chloropropoxy)-4-ethylsulfonylbenzoyl)-1,3-cyclohexanedione are to be excluded from the above definition.

Where $R^4$ is $OR^5$ and $R^5$ is hydrogen, the compounds of the formula (I) of the invention may, depending on external conditions, such as solvent and pH, occur in different tautomeric structures:

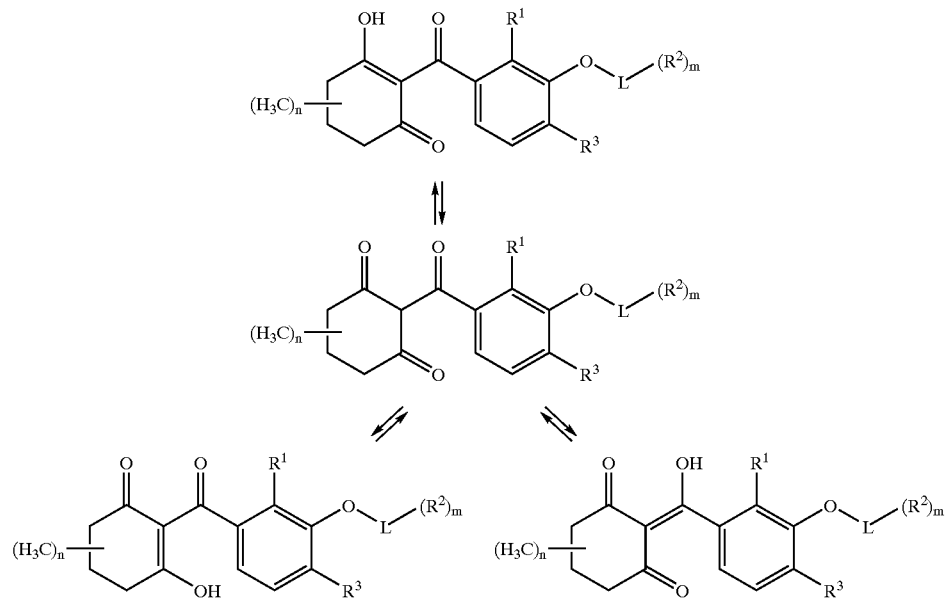

Depending on the nature of the substituents, the compounds of the formula (I) contain an acidic proton which may be removed by reaction with a base. Examples of suitable bases include hydrides, hydroxides, and carbonates of alkali metals and alkaline earth metals, such as lithium, sodium, potassium, magnesium, and calcium, and also ammonia and organic amines such as triethylamine and pyridine. Such salts are likewise provided by the invention.

In formula (I) and all subsequent formulae, alkyl radicals having more than two carbon atoms may be linear or branched. Alkyl radicals are, for example, methyl, ethyl, n- or i-propyl, n-, i-, t- or 2-butyl, pentyls, hexyls, such as n-hexyl, i-hexyl, and 1,3-dimethylbutyl. The saturated carbon chain L may likewise be linear or branched depending on the number of its carbon atoms. The m atoms from the group bromine, chlorine and fluorine that are attached to it may be located at any desired position in this chain.

Where a group is substituted plurally by radicals, this means that this group is substituted by one or more identical or different representatives of the radicals mentioned.

Depending on the nature and linkage of the substituents, the compounds of the formula (I) may be present in the form of stereoisomers. Where, for example, there are one or more asymmetric carbon atoms present, enantiomers and diastereomers may occur. Stereoisomers may be obtained from the synthesis mixtures by customary separation methods, such as by chromatographic separation techniques. Stereoisomers may likewise be prepared selectively through the use of stereoselective reactions using optically active reactants and/or auxiliaries. The invention also relates to all stereoisomers and mixtures thereof which are embraced by the formula (I) though not defined specifically.

Compounds of the formula (I) which have proven advantageous are those not present in salt form.

Compounds which have likewise proven advantageous are those wherein the substituents $R^1$ and $R^3$ have the same definition.

Preference is given to compounds of the formula (I) wherein
$R^2$ is bromine, chlorine or fluorine.

Likewise preferred compounds of the formula (I) are those wherein
L is a saturated carbon chain having 1, 2 or 3 carbon atoms;
$R^1$ is bromine, chlorine, fluorine, methyl, methylthio, methoxy or trifluoromethyl;
$R^3$ is bromine, chlorine, fluorine, methylsulfonyl or ethylsulfonyl, and
m is an integer from 1 to 7.

Particularly preferred compounds of the formula (I) are those wherein
$R^2$ is chlorine or fluorine and
$R^3$ is chlorine, fluorine, methylsulfonyl or ethylsulfonyl.

Very particularly preferred compounds of the formula (I) are those wherein
$R^1$ is bromine or chlorine;
$R^5$ is hydrogen, and
n is 0.

Further very particularly preferred compounds of the formula (I) are those wherein $R^1$ is chlorine.

Another group of very particularly preferred compounds of the formula (I) comprises those wherein $R^4$ is $OR^5$.

In all of the formulae below, the substituents and symbols have the same definition as described under formula (I), unless otherwise defined.

Compounds of the invention in which $R^5$ is hydrogen may be prepared, for example, in accordance with the method indicated in scheme 1, by base-catalyzed reaction of a benzoic halide (III) with a cyclohexanedione (II) in the presence of a cyanide source. Methods of this kind are described, for example, in EP-A 0 186 117.

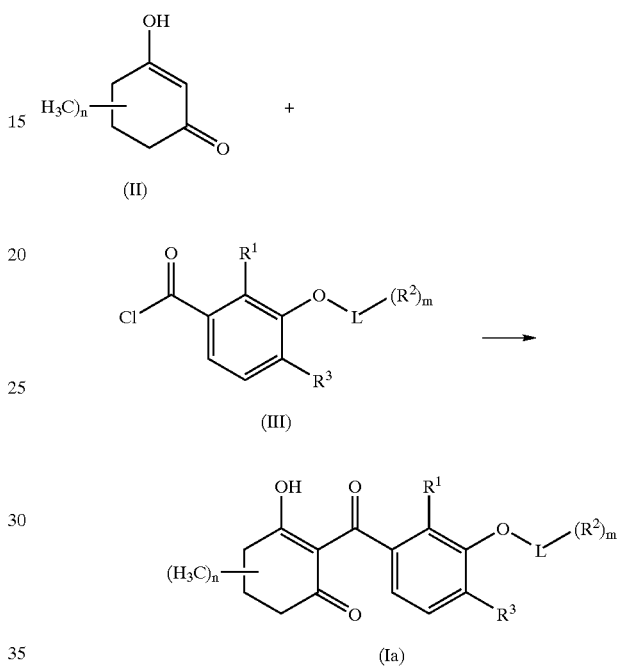

Scheme 1

Compounds of the invention in which $R^5$ has a meaning other than that of hydrogen are prepared in accordance with scheme 2, appropriately from the compounds obtainable by scheme 1, by halogenation of a suitable halogenating agent followed by base-catalyzed reaction of an alcohol $R^5$—OH or thiol $R^5$—SH. Methods of this kind are known, for example, from J. Fluorine Chem. 66 (1984) 1, 39–46 and Khim. Farm. Zh. 30 (1996) 2, 27–30.

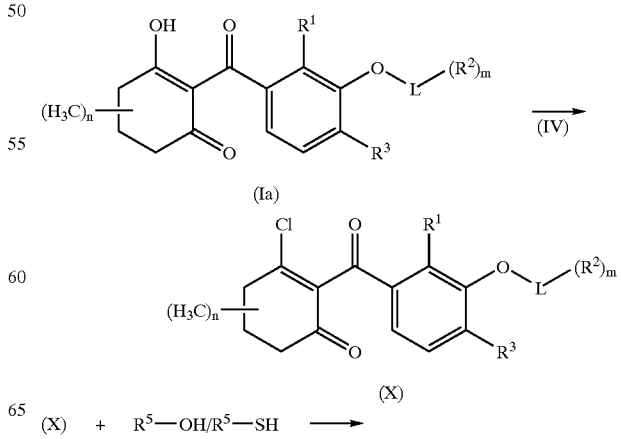

Scheme 2

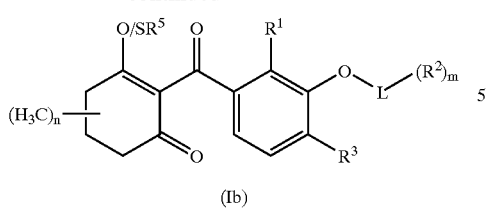

(Ib)

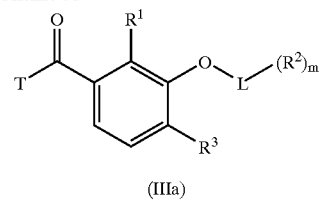

(IIIa)

The starting compounds used in the above schemes are either commercially available or can be prepared by methods which are known per se. The benzoyl chlorides (III), for example, may be prepared from the corresponding benzoic acids or benzoic esters of the formula (IIIa), in which T is hydroxyl or alkoxy. These benzoic acids and benzoic esters of the formula (IIIa) may be prepared, for example, in accordance with scheme 3 from the hydroxy derivatives (V) by reaction with compounds of the formula (VI), in which $M^1$ is a leaving group such as halogen, mesyl, tosyl, triflate or nonaflate. Methods of this kind are known, for example, from Houben-Weyl Volume 6/3, pp. 54 to 69, Volume 9, pp. 103 to 115, and Volume 11, p. 97.

Compounds of the formula (IIIa) in which T is hydroxyl or alkoxy may be prepared in accordance with scheme 5 by reacting compounds of the formula (VIII) in which $M^1$ is a leaving group such as halogen, mesyl, tosyl, triflate or nonaflate. Methods of this kind are known, for example, from WO 98/42648, and Houben Weyl Volume 6/3, pp. 75 to 78, Volume 9, pp. 103 to 105.

Scheme 5

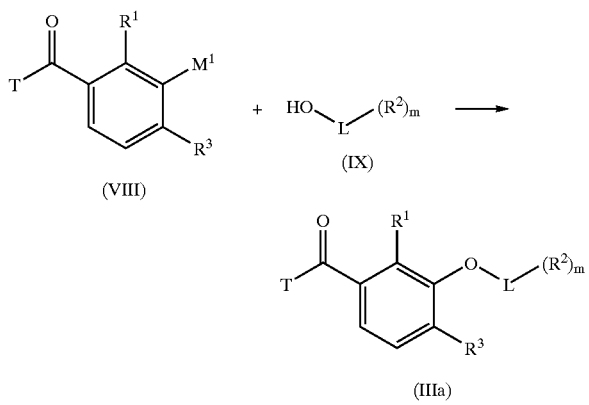

Scheme 3

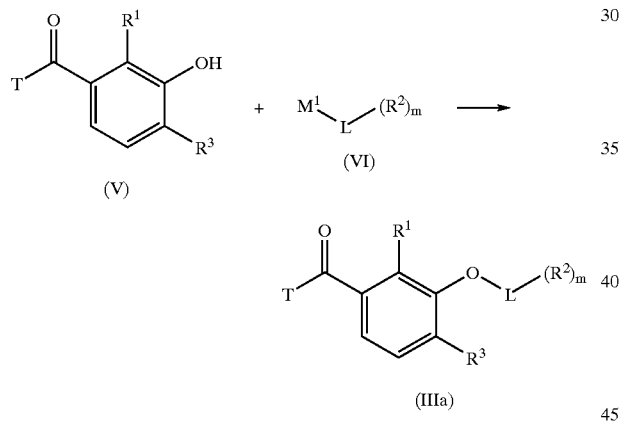

Compounds of the formula (IIIa) may also be prepared in accordance with scheme 4 by reacting compounds of the formula (V) with olefins of the formula (VII), in which L' is a saturated carbon chain having 1 to 2 carbon atoms and $R^{2a}$ and $R^{2b}$ are each chlorine or fluorine. Methods of this kind are described, for example, in Zh. Org. Khim. 27 (1991) 4, 781–788.

Scheme 4

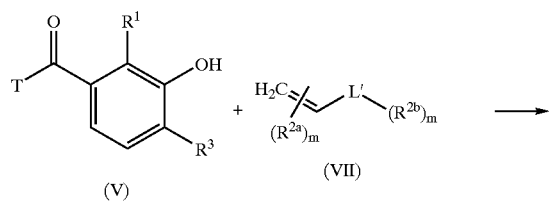

The compounds of the formula (I) according to the invention have an outstanding herbicidal activity against a broad spectrum of economically important monocotyledonous and dicotyledonous harmful plants. The active substances also effect good control of perennial weeds which produce shoots from rhizomes, root stocks or other perennial organs and which are difficult to control. In this context, it is immaterial whether the substances are applied before sowing, pre-emergence or post-emergence. Specifically, some representatives of the monocotyledonous and dicotyledonous weed flora which can be controlled by the compounds according to the invention may be mentioned by way of example, without a restriction to certain species being intended to take place as a result of the mention. Amongst the monocotyledonous weed species, those on which the active substances act efficiently are, for example, Avena, Lolium, Alopecurus, Phalaris, Echinochloa, Digitaria, Setaria and Cyperus species from the annual group and, among the perennial species, Agropyron, Cynodon, Imperata and Sorghum and also perennial Cyperus species. In the case of dicotyledonous weed species, the spectrum of action extends to species such as, for example, Galium, Viola, Veronica, Lamium, Stellaria, Amaranthus, Sinapis, Ipomoea, Sida, Matricaria and Abutilon among the annuals and Convolvulus, Cirsium, Rumex and Artemisia in the case of the perennial weeds. Harmful plants occurring under the specific cultivation conditions of rice such as, for example, Echinochloa, Sagittaria, Alisma, Eleocharis, Scirpus and Cyperus, are also outstandingly well controlled by the active substances according to the invention. If the compounds according to the invention are applied to the soil surface before germination, then the weed seedlings are either prevented completely from emerging or the weeds grow until they have reached the cotyledon stage, but then their growth stops and they finally die completely after three to four weeks have elapsed. When the active substances are applied post-emergence to the green parts of the plants, growth also stops drastically a very short time after the treatment and the weed plants remain at the stage of growth at the time of application, or they die completely after a certain time, so that in this manner competition by the weeds, which is harmful to the crop plants, is eliminated at a very early stage and in a sustained manner. In particular, the compounds of the invention exhibit an outstanding action against Amaranthus retroflexus, Avena sp., Echinochloa sp., *Cyperus serotinus, Lolium multiflorum, Setaria viridis, Sagittaria pygmaea, Scirpus juncoides*, Sinapis sp., and *Stellaria media*.

Although the compounds according to the invention have excellent herbicidal activity against monocotyledonous and dicotyledonous weeds, crop plants of economically important crops such as wheat, barley, rye, rice, maize, sugar beet, cotton, and soybeans are damaged only to an insignificant extent or not at all. They exhibit outstanding tolerance, in particular by wheat, maize, and rice. For these reasons, the present compounds are very highly suitable for selectively controlling unwanted vegetation in stands of agriculturally useful plants or of ornamental plants.

On account of their herbicidal properties, the active substances can also be employed for controlling harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or plant pathogens, such as certain insects or microorganisms such as fungi, bacteria or viruses. Other particular properties relate, for example, to the harvested material with respect to quantity, quality, storability, composition and specific constituents. Thus, transgenic plants with an increased starch content or in which the quality of the starch is altered, or those having a different fatty acid composition of the harvested material, are known.

The compounds of the formula (I) according to the invention or their salts are preferably used in economically important transgenic crops of useful plants and ornamentals, e.g. of cereals such as wheat, barley, rye, oats, millet, rice, cassava and maize, or else crops of sugar beet, cotton, soybeans, oilseed rape, potatoes, tomatoes, peas and other types of vegetable. The compounds of the formula (I) can preferably be employed as herbicides in crops of useful plants which are resistant, or have been made resistant by recombinant methods, to the phytotoxic effect of herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of recombinant modifications of crop plants for the purpose of modifying the starch synthesized in the plants (for example WO 92/11376, WO 92/14827, WO 91/19806), transgenic crop plants which are resistant to certain herbicides of the glufosinate type (cf., for example, EP-A0242236, EP-A-242246) or of the glyphosate type (WO 92/00377) or of the sulfonylurea type (EP-A0257993, U.S. Pat. No. 5,013,659), transgenic crop plants, for example cotton, with the capability of producing *Bacillus thuringiensis* toxins (*Bt* toxins) which make the plants resistant to certain pests (EP-A-0142924, EP-A-0193259), transgenic crop plants having a modified fatty acid composition (WO 91/13972).

A large number of molecular-biological techniques with which novel transgenic plants with modified properties can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Kione" [Genes and Clones], VCH Weinheim 2nd Edition 1996 or Christou, "Trends in Plant Science"1 (1996) 423–431).

To carry out such recombinant manipulations, nucleic acid molecules which permit a mutagenesis or a sequence modification by recombination of DNA sequences can be introduced into plasmids. For example, it is possible with the aid of the abovementioned standard methods to carry out base exchanges, to remove subsequences or to add natural or synthetic sequences. Adapters or linkers may be added in order to link the DNA fragments to each other.

For example, plant cells with a reduced activity of a gene product can successfully be generated by expressing at least one suitable antisense RNA, a sense RNA to achieve a cosuppression effect or by expressing at least one suitably constructed ribozyme which specifically cleaves transcripts of the abovementioned gene product.

To this end, it is possible to use firstly DNA molecules which encompass all of the coding sequence of a gene product including any flanking sequences which may be present and secondly DNA molecules which only encompass parts of the coding sequence, it being necessary for these parts to be of sufficient length to cause an antisense effect in the cells. Also possible is the use of DNA sequences which have a high degree of homology with the coding sequences of a gene product but which are not entirely identical thereto.

When expressing nucleic acid molecules in plants, the protein synthesized may be localized in any compartment of the plant cell. However, to achieve localization in a particular compartment, it is possible for example to link the coding region with DNA sequences which guarantee localization in a certain compartment. Sequences of this type are known to the person skilled in the art, (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Transgenic plants are thus obtainable which have modified properties as a result of overexpression, suppression or inhibition of homologous (=natural) genes or gene sequences, or expression of heterologous (=foreign) genes or gene sequences.

When the active substances according to the invention are used in transgenic crops, effects which are specific for application in the particular transgenic crop, for example a modified or specifically widened spectrum of action which can be controlled, altered application rates which can be employed for application, preferably good combining ability with the herbicides, to which the transgenic crop is in resistant, and an effect on growth and yield of the transgenic crop plants, occur in addition to the effects against harmful plants which can be observed in other crops. Subject matter of the invention is therefore also the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted influencing of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. Also provided by the invention, therefore, are herbicidal compositions comprising compounds of the formula (I). The compounds of the formula (I) can be formulated in various ways, depending on the prevailing biological and/or physicochemical parameters. Examples of suitable formulations which are possible include wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie", Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss. Verlagsgesell., Stuttgart 1976; Winnacker-Küchler, "Chemische Technologie", Volume 7, C. Hanser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been listed for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see for example methods in "Spray-Drying Handbook" 3rd Ed. 1979, G. Goodwin Ltd., London; J. E. Browning, "Agglomeration", Chemical and Engineering 1967, pages 147 et seq.; "Perry's Chemical Engineers Handbook", 5th Ed., McGraw-Hill, New York 1973, pp. 8–57.

For further details on the formulation of crop protection products see, for example G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Known herbicides which can be combined with the compounds of the formula (I) Include, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-trifluoromethyl)-phenoxy]-2-nitrophenyl]-2-methoxyethylidene]amino]oxy]acetic acid and its methyl ester, alachlor, alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor, butamifos; butenachlor; buthidazole; butralin; butylate; cafenstrole (CH-900); carbetamide; cafentrazone (ICI-A0051); CDM, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecolmethyl; chloridazon; chlorimuron ethyl; chlomitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flampropmethyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S482); flumipropyn; flupoxam (KNW-739); fluorodifen; fluoroglycofen-ethyl; flupropacil (UBIC-4243); fluridone; flurochloridone; fluroxypyr, flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenzmethyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor, metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatves for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole: secbumeton; sethoxydim; siduron; simazine; simetryn;

SN 106279, i.e. 2-[[7-[2-chloro-4-(trifluoromethyl)phenoxy]-2-naphthalenyl]oxy]propanoic acid and its methyl ester; sulfentrazon (FMC97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; triallate; triasulfuron; triazofenamide; tribenuron-methyl; triclopyr; tridiphane; trietazine; trifluralin; triflusulfuron and esters (for example methyl ester, DPX66037); trimeturon; tsitodef; vernolate; WL 110547, i.e. 5-phenoxy-1-[3-trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulatons, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use.

The required application rate of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples below illustrate the invention.

A. Chemical Examples

The ethyl 2,4-dibromo-3-hydroxybenzoate starting compound was prepared in accordance with U.S. Pat. No. 5,026,896, 2-chloro-3-hydroxy-4-ethylsulfonylbenzoic acid in accordance with U.S. Pat. No. 709,006. 2,2,3,3-tetrafluompropyl perfluorobutanesulfonate and 2,2,2-trifluoromethyl perfluorobutanesulfonate were prepared in accordance with J. Org. Chem. USSR 14 (1978) 808–809.

The abbreviation RT stands for room temperature.

1. Preparation of 2-(2-chloro-3-(2,2,3,3-tetrafluoropropyloxy)-4-ethylsulfonylbenzoyl)cyclohexane-1,3-dione Step 1: Methyl 2-chloro-3-hydroxy-4-ethylsulfonylbenzoate 33.0 g (124.7 mmol) of 2-chloro-3-hydroxy-4-ethylsulfonylbenzoic acid were dissolved in 1300 ml of methanol. 174 ml (3263 mmol) of conc. $H_2SO_4$ were added dropwise and the mixture was heated under reflux for 5 h. The reaction mixture was concentrated and the residue was taken up in methylene chloride. It was washed with water, dried over $Na_2SO_4$ and concentrated to completion. This gave methyl 2-chloro-3-hydroxy-4-ethylsulfonylbenzoate as a viscous yellow oil.

Yield: 28.23 g (81% of theory).
$^1$H-NMR: δ [CDCl3] 1.32 (t, 3H), 3.24 (q, 2H), 3.96 (s, 3H), 7.38 (d, 1H), 7.65 (d, 1H).
$R_f$ (ethyl acetate): 0.45.

Step 2: Methyl 2-chloro-3-(2,2,3,3-tetrafluoropmpyloxy)-4-ethylsulfonylbenzoate 1.200 g (4.3 mmol) of potassium tert-butoxide and 1.917 g (4.3 mmol) of 2,2,3,3-tetrafluoropropyl perfluorobutanesulfonate were introduced into 30 ml of DMF in a vessel. At RT, 1200 g (4.3 mol) of methyl 2-chloro-3-hydroxy-4-ethylsulfonylbenzoate were added and the mixture was then heated at 120° C. for 7 h. It was subsequently introduced into water and subjected to extraction with diisopropyl ether. The combined organic phases were washed with water, dried over $Na_2SO_4$, and concentrated. Drying under an oil pump vacuum gave methyl 2-chloro-3-(2,2,3,3-tetrafluoropropyloxy)-4-ethylsulfonylbenzoate as a brown oil.

Yield: 1.60 g (95% of theory).
$^1$H-NMR: δ [CDCl3] 1.27 (t, 3H), 3.43 (q, 2H), 4.00 (s, 3H), 4.66 (m, 2H), 6.07 (m, 1H), 7.76 (d, 1H), 7.96 (d, 1H).
$R_f$ (ethyl acetate): 0.73.

Step 3: 2-Chloro-3-(2,2,3,3-tetrafluoropropyloxy)-4-ethylsulfonylbenzoic Acid 1.600 g (4.07 mmol) of methyl 2-chloro-3-(2,2,3,3-tetrafluoropropyloxy)-4-ethylsulfonylbenzoate were dissolved in a mixture of 20 ml of THF and 20 ml of water, and with 0.218 g (5.50 mmol) of sodium hydroxide was added. The mixture was stirred at RT for 12 h and concentrated. The residue was taken up in water and admixed with 6 N HCl. The precipitate was filtered off with suction and dried. This gave 2-chloro-3-(2,2,3,3-tetrafluoropropyloxy)-4-ethylsulfonylbenzoic acid in the form of a white solid.

Yield: 1.45 g (89% of theory).
$^1$H-NMR: δ [d6-DMSO] 1.11 (t, 3H), 3.49 (q, 2H), 1.62 (m, 4H), 4.62 (m, 2H), 6.76 (m, 1H), 7.80 (d, 1H), 7.89 (d, 1H).
Melting point: 163–166° C.

Step 4: ((3-Oxo-1-cyclohexenyl)-2-chloro-3-(2,2,3,3-tetrafluoropropyloxy)-4-ethylsulfonyl)benzoate 0.710 g (1.90 mmol) of 2-chloro-3-(2,2,3,3-tetrafluoropropyloxy)-4-ethylsulfonylbenzoic acid, 0.231 g (2.10 mmol) cyclohexane-1,3-dione, 0.403 g (2.10 mmol) of N'-3-dimethylaminopropyl)-N-ethylcarbodiimide hydrochloride and 0.002 g of dimethylaminopyridine were stirred in 10 ml of $CH_2Cl_2$ at RT for 10 h. The mixture was then diluted with $CH_2Cl_2$ and washed with 0.5 N HCl, with water, with saturated $NaHCO_3$ solution, and with water again. Drying of the combined organic phases over $Na_2SO_4$ and complete concentration gave ((3-oxo-1-cyclohexenyl)-2-chloro-3-(2,2,3,3-tetrafluoropropyloxy)-4-ethylsulfonyl)benzoate in the form of a brown resin which was sufficiently pure for the subsequent reaction.

Yield: 0.720 g.
$^1$H-NMR: δ [CDCl3] 1.27 (t, 3H), 2.16 (m, 2H), 2.49 (m, 2H), 2.70 (m, 2H), 3.44 (q, 2H), 4.66 (m, 2H), 6.05 (m, 1H), 6.08 (s, 1H), 7.86 (d, 1H), 8.02 (d, 1H).
$R_f$ (ethyl acetate): 0.65.

Step 5: 2-(2-Chloro-3-(2,2,3,3-taetrafluoropyloxy)-4-ethylsulfonylbenzoyl)cyclohexane-1,3-dione 0.690 g (1.50 mmol) of ((3-oxo-1-cyclohexenyl)-2-chloro-3-(2,2,3,3-tetrafluoropropyloxy)-4-ethylsulfonyl)benzoate was dissolved in 10 ml of acetonitrile. 3 drops of acetone cyanohydrin and 0.258 g (2.60 mmol) of $NEt_3$ were added. The mixture was stirred at RT for 2 h and then 0.044 g (0.70 mmol) of KCN was added. After a further 10 h at RT, the mixture was concentrated to completion, the residue was taken up in water, and 6 N hydrochloric acid was added. The product was then extracted with $CH_2Cl_2$. Drying of the combined organic phases over $Na_2SO_4$, complete concentration and chromatography on reversed-phase silica gel (eluent: acetonitrile/water gradient) gave 2-(2-chloro-3-(2,2,3,3-tetrafluoropropyloxy)-4ethylsulfonylbenzoyl)cyclohexane-1,3-dione in the form of a viscous colorless oil.

Yield: 0.198 g (28% of theory).

$^1$H-NMR: δ [CDCl3] 1.31 (t, 3H), 2.09 (m, 2H), 2.59 (m, 2H), 2.84 (m, 2H), 3.40 (q, 2H), 4.64 (m, 2H), 6.06 (m, 1H), 7.16 (d, 1H), 7.95 (d, 1H).

$R_f$ (ethyl acetate): 0.23.

2. Preparation of 2,4-dibromo-3-(2,2,2-trifluoroethoxy)cyclohexane-1,3-dione

Step 1: Ethyl 2,4-dibromo-3-(2,2,2-trifluoroethoxy) benzoate 0.416 g (3.70 mmol) of potassium tert-butoxide and 1.200 g (3.70 mmol) of ethyl 2,4-dibromo-3-hydroxybenzoate were introduced into 15 ml of DMF in a vessel. At RT, 1.490 g (3.70 mmol) of 2,2,2-trifluoropropyl perfluorobutanesulfonate were added and the mixture was heated at 120° C. for 6 h. Thereafter it was introduced into water and subjected to extraction with diisopropyl ether. The combined organic phases were washed with water, dried over $Na_2SO_4$ and concentrated to completion. Drying under an oil pump vacuum gave ethyl 2,4-dibromo-3-(2,2,2-trifluoroethoxy) benzoate as a brown oil.

Yield: 1.42 g (79% of theory).

$^1$H-NMR: δ [CDCl3] 1.20 (t, 3H), 4.32–4.46 (m, 2H+2H), 7.45 (d, 1H), 7.60 (d, 1H).

$R_f$ (ethyl acetate): 0.82.

Step 2: 2,4-Dibromo-3-(2,2,2-trifluoroethoxy)benzoic acid 1.380 g (3.40 mmol) of ethyl 2,4-dibromo-3-(2,2,2-trifluoroethoxy)benzoate were dissolved in a mixture of 15 ml of THF and 15 ml of water, and 0.150 g (3.47 mmol) of NaOH was added. The mixture was stirred at RT for 12 h and concentrated to completion. The residue was taken up in water, and 6 N HCl was added. The precipitate was filtered off with suction and dried. This gave 2-chloro-2,4-dibromo-3-(2,2,2-trifluoroethoxy)benzoic acid in the form of a white solid.

Yield: 1.01 g (79% of theory).

$^1$H-NMR: δ [d6-DMSO] 4.6 (m, 2H), 7.46 (d, 1H), 7.80 (d, 1H).

Melting point: 148–151° C.

Step 3: ((3-Oxo-1-cyclohexenyl)-2,4-dibromo-3-(2,2,2-trifuoroethoxy))benzoate 0.490 g (1.30 mmol) of 2,4-dibromo-3-(2,2,2-trifluoroethoxy)benzoic acid, 0.160 g (1.40 mmol) of cyclohexane-1,3-dione, 0.279 g (1.40 mmol) of N'-(3-dimethylaminopropyl)-N-ethylcarbodiimide hydrochloride and 0.002 g of dimethylaminopyridine were stirred in 10 ml of $CH_2Cl_2$ at RT for 30 h. The mixture is, was then diluted with $CH_2Cl_2$ and washed with 0.5 N HCl, with water, with saturated $NaHCO_3$ solution, and with water again. Drying of the combined organic phases over $Na_2SO_4$ and complete concentration gave ((3-oxo-1-cyclohexenyl)-2,4-dibromo-3-(2,2,2-trifluoroethoxy))benzoate in the form of a yellow resin which was sufficiently pure for the subsequent reaction.

Yield: 0.37 g.

$^1$H-NMR: δ [CDCl3] 2.14 (m, 2H), 2.46 (m, 2H), 2.70 (m, 1H), 4.42 (m, 2H), 6.04 (s, 1H), 7.54 (d, 1H), 7.66 (d, 1H).

$R_f$ (ethyl acetate): 0.68.

Step 4: 2,4-Dibromo-3-(2,2,2-trifluoroethoxy)cyclohexane-1,3-dione 0.340 g (0.70 mmol) of ((3-oxo-1-cydohexenyl)-2,4-dibromo-3-(2,2,2-trifluoroethoxy))benzoate was dissolved in 10 ml of acetonitrile. 3 drops of acetone cyanohydrin and 0.128 g (1.30 mmol) of triethylamine were added. The mixture was stirred at RT for 2 h, and then 0.022 g (0.30 mmol) of KCN was added. After a further 10 h at RT, the mixture was concentrated to completion and the residue was taken up in water and admixed with 6 N hydrochloric acid. The product was then extracted with $CH_2Cl_2$. Drying of the organic phases over $Na_2SO_4$, complete concentration and chromatography on silica gel (eluent: toluene/THF) gave 2,4-dibromo-3-(2,2,2-trifluoroethoxy)cyclohexane-1,3-dione in the form of a colorless oil.

Yield: 0.143 g (42% of theory).

$^1$H-NMR: δ [CDCl3] 2.04 (m, 2H), 2.43 (m, 2H), 2.78 (d, 2H), 4.20 (m, 2H), 6.85 (2, 1H), 7.59 (d, 1H).

$R_f$ (ethyl acetate): 0.40.

The examples listed in the tables below were prepared in analogy to methods specified above or are obtainable in analogy to abovementioned methods. In these tables, the abbreviations have the following meanings:

Et = Ethyl    Me = Methyl    m.p = Melting point

TABLE A

Compounds of the formula (I) of the invention in which the substituents and symbols have the following definitions:
$R^4$ = OH
n = 0

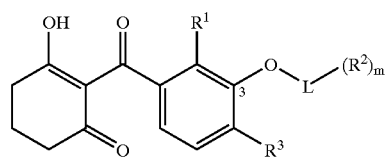

(I)

| No. | $R^1$ | —L—$(R^2)_m$ | $R^3$ | Physical data $R_f$ (ethylacetate) |
|---|---|---|---|---|
| 1.1 | Cl | $OCH_2CF_2CF_2H$ | $SO_2Et$ | 0.23 |
| 1.2 | Br | $OCH_2CF_3$ | Br | 0.40 |
| 1.3 | Cl | $OCF_2H$ | Cl | |
| 1.4 | Cl | $OCF_2(CHF)CF_3$ | Cl | |
| 1.5 | Cl | $OCH_2CF_2H$ | Cl | 0.45 |
| 1.6 | Cl | $OCH_2CH_2Cl$ | Cl | |
| 1.7 | Cl | $OCH_2CHCl_2$ | Cl | |
| 1.8 | Cl | $OCH_2CF_3$ | Cl | 0.32 |
| 1.9 | Cl | $OCF_2Cl$ | Cl | |
| 1.10 | Cl | $OCF_2Br$ | Cl | |
| 1.11 | Cl | $OCH_2CH_2CF_3$ | Cl | 0.41 |
| 1.12 | Cl | $OCF_2H$ | $SO_2Me$ | |
| 1.13 | Br | $OCF_2H$ | Br | |
| 1.14 | Cl | $OCH_2CF_2CF_2H$ | Cl | 0.43 |
| 1.15 | Cl | $OCH_2CCl_3$ | Cl | |
| 1.16 | Cl | $OCH_2C_3F_7$ | Cl | 0.38 |
| 1.17 | Cl | $OCH_2CCl_3$ | $SO_2Et$ | |
| 1.18 | Cl | $OCH_2(CHCl)CH_2Cl$ | $SO_2Et$ | |
| 1.19 | Br | $OCH_2C_2F_5$ | Br | 0.38 |
| 1.20 | Cl | $OCH_2CF_2H$ | $SO_2Me$ | |
| 1.21 | Cl | $OCH_2CF_3$ | $SO_2Me$ | 0.07 |
| 1.22 | Cl | $OCH_2CF_2CF_2H$ | $SO_2Me$ | 0.16 |
| 1.23 | Cl | $OCF_2(CHF)CF_3$ | $SO_2Et$ | |
| 1.24 | Cl | $OCH_2C_3F_7$ | $SO_2Me$ | 0.29 |
| 1.25 | Cl | $OCH_2CH_2CF_3$ | $SO_2Me$ | |
| 1.26 | Cl | $OCF_2(CHF)CF_3$ | $SO_2Me$ | |
| 1.27 | Cl | $OCH_2CH_2Cl$ | $SO_2Me$ | |
| 1.28 | Cl | $OCH_2CHCl_2$ | $SO_2Me$ | |
| 1.29 | Cl | $OCH_2CCl_3$ | $SO_2Me$ | |
| 1.30 | Cl | $OCH_2(CHCl)CH_2Cl$ | $SO_2Me$ | |
| 1.31 | Cl | $OCF_2Cl$ | $SO_2Me$ | |
| 1.32 | Cl | $OCH_2C_2F_5$ | $SO_2Me$ | 0.25 |
| 1.33 | Cl | $OCH_2CH_2Cl$ | $SO_2Et$ | |
| 1.34 | Cl | $OCF_2H$ | $SO_2Et$ | |
| 1.35 | Cl | $OCH_2CF_2H$ | $SO_2Et$ | 0.24 |
| 1.36 | Cl | $OCH_2CHCl_2$ | $SO_2Et$ | |
| 1.37 | Br | $OCF_2(CHF)CF_3$ | Br | |
| 1.38 | Cl | $OCH_2CF_3$ | $SO_2Et$ | 0.27 |
| 1.39 | Cl | $OCH_2C_2F_5$ | Cl | 0.45 |
| 1.40 | Br | $OCH_2CH_2CF_3$ | Br | |
| 1.41 | Cl | $OCH_2CH_2CF_3$ | $SO_2Et$ | 0.53 |

TABLE A-continued

Compounds of the formula (I) of the invention in which the substituents and symbols have the following definitions:
$R^4 = OH$
$n = 0$

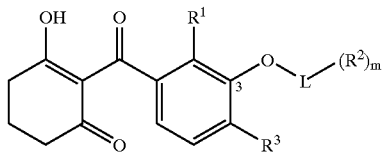

(I)

| No. | $R^1$ | —L—$(R^2)_m$ | $R^3$ | Physical data $R_f$ (ethylacetate) |
|---|---|---|---|---|
| 1.42 | Br | OCH$_2$CH$_2$Cl | Br | |
| 1.43 | Br | OCH$_2$CF$_2$H | Br | 0.41 |
| 1.44 | Cl | OCH$_2$C$_2$F$_5$ | SO$_2$Et | 0.22 |
| 1.45 | Br | OCF$_2$Cl | Br | |
| 1.46 | Cl | OCF$_2$Cl | SO$_2$Et | |
| 1.47 | Cl | OCF$_2$Br | SO$_2$Et | |
| 1.48 | Cl | OCH$_2$CF$_2$Br | SO$_2$Et | |
| 1.49 | Cl | OCH$_2$C$_3$F$_7$ | SO$_2$Et | 0.23 |
| 1.51 | Br | OCH$_2$CHCl$_2$ | Br | |
| 1.52 | Br | OCH$_2$CCl$_3$ | Br | |
| 1.53 | Br | OCH$_2$C$_3$F$_7$ | Br | 0.29 |
| 1.54 | Br | OCH$_2$CF$_2$CF$_2$H | Br | 0.42 |

B. Formulation Examples

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetter and dispersant and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to over 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I), 10 parts by weight of calcium lignosulfonate,
5 parts by weight of sodium lauryl sulfate,
3 parts by weight of polyvinyl alcohol and
7 parts by weight of kaolin, grinding the mixture in a pinned-disk mill and granulating the powder in a fluidized bed by spraying on water as granulating fluid.

Water-dispersible granules are also obtained by homogenizing and precomminuting 25 parts by weight of a compound of the formula (I), 5 parts by weight of sodium 2,2'-dinaphthylmethane-6,6'-disulfonate,
2 parts by weight of sodium oleoylmethyltaurate,
1 parts by weight of polyvinyl alcohol,
17 parts by weight of calcium carbonate and
50 parts by weight of water in a colloid mill, subsequently grinding the mixture in a bead mill and atomizing and drying the suspension obtained in a spray tower by means of a single-substance nozzle.

C. Biological Examples

1. Herbicidal action post-emergence

Seeds of mono- and dicotyledonous weeds are put into sandy loam in cardboard pots, covered with soil and grown in the greenhouse under good growth conditions. Two to three weeks after sowing, the test plants are treated in the three-leaf stage. The compounds according to the invention, which are formulated as wettable powders or as emulsion concentrates, are sprayed onto the surface of the green plant parts at a water application rate of 600 to 800 l/ha (converted). After the test plants have been left to stand in the greenhouse for 3 to 4 weeks under optimal growth conditions, the action of the compounds is scored in comparison with prior art compounds. As the results of these comparison tables show, the compounds of the invention selected show outstanding activity against a broad spectrum of economically important mono- and dicotyledonous harmful plants.

4. Crop Plant Tolerance

In further experiments in the greenhouse, seeds of barley and mono- and dicotyledonous weeds are put in sandy loam, covered with soil and placed in the greenhouse until the plants have developed two to three true leaves. They are then treated with the compounds of the formula (I) according to the invention and, comparatively, with the prior art compounds as described under item 1 above. Four to five weeks after application and after the plants have remained in the greenhouse, it is found by means of visual scoring that the compounds according to the invention exhibit outstanding tolerance by important crop plants, in particular wheat, maize, and rice.

What is claimed is:

1. A compound of the formula (I) or salt thereof

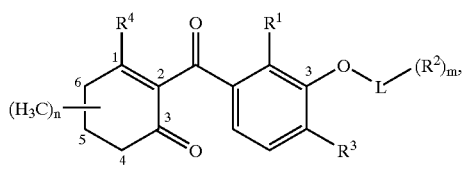

in which

L is a saturated carbon chain having 1, 2, 3 or 4 carbon atoms;

$R^1$ is iodine, bromine, chlorine, fluorine, $C_1$–$C_4$ alkyl, $C_1$–$C_4$ alkylthio, $C_1$–$C_4$ alkoxy or $C_1$–$C_4$ haloalkyl;

$R^2$ is bromine, chlorine, iodine or fluorine;

$R^3$ is bromine, chlorine, fluorine, cyano, nitro, $C_1$–$C_4$ alkyl, methylsulfonyl or ethylsulfonyl;

$R^4$ is $OR^5$ or $SR^5$;

$R^5$ is hydrogen, $C_1$–$C_4$ alkyl, $C_2$–$C_4$ alkenyl, $C_2$–$C_4$ alkynyl, benzyl or phenyl;

m is an integer from 1 to 9, and n is 0, 1 or 2, with the proviso that e) the radical O—L—$(R^2)_m$ is not to be trifluoromethoxy, and f) the compounds 2-(3-(2,3-dibromopropoxy)-2-chloro-4-ethylsulfonylbenzoyl-1,3-cyclohexanedione and 2-(2-chloro-3-(3-chloropropoxy)-4-ethylsulfonyl-benzoyl)-1,3-cyclohexanedione are to be excluded from the above definition.

2. A compound as claimed in claim 1, wherein $R^2$ is bromine, chorine or fluorine.

3. A compound as claimed in claim 1, wherein

L is a saturated carbon chain having 1, 2 or 3 carbon atoms;

$R^1$ is bromine, chorine, fluorine, methyl, methylthio, methoxy or triflouromethyl;

$R^3$ is bromine, chlorine, fluorine, methylsulfonyl or ethylsulfonyl, and m is an integer from 1 to 7.

4. A compound as claimed in claim 1, wherein $R^2$ is chlorine or fluorine and $R^3$ is chlorine, fluorine, methylsulfonyl or ethylsulfonyl.

5. A compound as claimed in claim 1, wherein $R^1$ is bromine or chlorine;

$R^5$ is hydrogen, and n is 0.

6. A compound as claimed in claim 1, wherein $R^1$ and $R^3$ have the same definition.

7. A compound as claimed in claim 1, wherein $R^1$ is chlorine.

8. A herbicidal composition comprising a herbicidally active amount of at least one compound of the formula (I) as claimed in claim 1.

9. A herbicidal composition as claimed in claim 8 in a mixture with formulating auxiliaries.

10. A method of controlling unwanted plants which comprises applying an effective amount of at least one compound of the formula (I) as claimed in claim 1 or of a herbicidal composition as claimed in claim 8 or 9 to the plants or to the site of the unwanted plant growth.

11. A method of controlling unwanted plants in crops of useful transgenic plants which comprises applying an effective amount of at least one compound of the formula (I) as claimed in claim 1.

12. A method of controlling unwanted plants in crops of useful transgenic plants which comprises applying an effective amount of a herbicidal composition as claimed in claim 8 to the plants or to the site of the unwanted plant growth.

13. A method of controlling unwanted plants in crops of useful transgenic plants which comprises applying an effective amount of a herbicidal composition as claimed in claim 9 to the plants or to the site of the unwanted plant growth.

* * * * *